United States Patent
Poynard (10) Patent No.: US 7,225,080 B2
(45) Date of Patent: *May 29, 2007

(54) DIAGNOSIS METHOD OF INFLAMMATORY, FIBROTIC OR CANCEROUS DISEASE USING BIOCHEMICAL MARKERS

(75) Inventor: Thierry Poynard, Paris (FR)

(73) Assignee: Assistance Publique-Hopitaux de Paris (AP-HP), Paris (FR)

( * ) Notice: Subject to any disclaimer, the term of this patent is extended or adjusted under 35 U.S.C. 154(b) by 488 days.

This patent is subject to a terminal disclaimer.

(21) Appl. No.: 10/650,260

(22) Filed: Aug. 27, 2003

(65) Prior Publication Data

US 2004/0039553 A1    Feb. 26, 2004

Related U.S. Application Data

(63) Continuation of application No. 09/687,459, filed on Oct. 13, 2000, now Pat. No. 6,631,330.

(30) Foreign Application Priority Data

Aug. 21, 2000   (EP)   .................................. 00402326

(51) Int. Cl.
*G06F 19/00* (2006.01)
*G01N 33/573* (2006.01)

(52) U.S. Cl. .......................................... 702/19; 435/7.4

(58) Field of Classification Search ...................... None
See application file for complete search history.

(56) References Cited

U.S. PATENT DOCUMENTS 6,631,330 B1 * 10/2003 Poynard ....................... 702/19

OTHER PUBLICATIONS

Poynard and Bedossa, "Age and platelet count: a simple index for predicting the presence of histological lesions in patients with antibodies to hepatitis C virus." METAVIR and CLINIVIR Cooperative Study Groups. *J. Viral Hepat.* 4(3):199-208 (May 1997).

* cited by examiner

*Primary Examiner*—John S. Brusca
(74) *Attorney, Agent, or Firm*—Needle & Rosenberg, PC (57) ABSTRACT

The present invention is drawn to a new diagnosis method for detecting the extend of a inflammatory, fibrotic or cancerous disease in a patient, in particular liver fibrosis, in particular in a patient infected with hepatitis C virus, by using the serum concentration of easily detectable biological markers. The invention is also drawn to diagnosis kits for the implementation of the method.

16 Claims, 6 Drawing Sheets

DIAGNOSIS METHOD OF INFLAMMATORY, FIBROTIC OR CANCEROUS DISEASE USING BIOCHEMICAL MARKERS

CROSS-REFERENCE TO RELATED APPLICATIONS

This application is a continuation of application Ser. No. 09/687,459, filed Oct. 13, 2000 now U.S. Pat. No. 6,631,330, which claims priority to European Patent Application No. 00402326.3, filed Aug. 21, 2000, which applications are hereby incorporated herein by reference in their entirety.

FIELD OF THE INVENTION

The present invention is drawn to a new diagnosis method for detecting the extend of a inflammatory, fibrotic or cancerous disease in a patient, in particular liver fibrosis, in particular in a patient infected with hepatitis C virus, by using the serum concentration of easily detectable biological markers. The invention is also drawn to diagnosis kits for the implementation of the method.

BACKGROUND OF THE INVENTION

Liver biopsy is considered as mandatory for the management of patients infected by the hepatitis C virus (HCV), particularly for the staging of fibrosis (1–4). For patients and general practitioner it can be considered as an aggressive procedure (5–6). Numerous studies have shown significant predictive values of several markers for the diagnosis of cirrhosis (6–15) but none for the diagnosis of earlier stage as few septa (beginning of bridging fibrosis), prospectively in a large population infected only by HCV virus.

It is nevertheless important to be able to detect these early stages in the development of liver pathology, in order to improve the patient treatment, and the follow-up of the disease. As liver biopsy is still an invasive procedure, it could be advantageous to have a fast and easy to perform test that would give a good predictive value of the level of fibrosis in the patient.

After infection by the hepatitis C virus, the evolution of the disease can lead to fibrosis, and later to cirrhosis. The liver biopsy allows for the determination of the stage of the fibrosis, but also the presence of liver necroinflammatory lesions. The intensity and activity of such lesions, in complement to the degree of fibrosis, are acknowledged by physicians as an important factor for diagnosis and prognosis of the evolution of the disease, and in order to determine the type of treatment to administrate.

There is therefore a need to develop a diagnosis method that would give a good predictive value of the presence (or the absence) of fibrosis and/or lesions in a patient, and that would be reliable enough to reduce the need of liver biopsy.

SUMMARY OF THE INVENTION

The present invention provides a method of diagnosis that assesses prospectively the predictive value of a combination of simple serum biochemical markers for the diagnosis of an inflammatory, fibrotic or cancerous disease, in particular in the liver of a patient where it is well suited for diagnosis of significant fibrosis (from few septa to cirrhosis) and/or liver necroinflammatory lesions. With the reach of high positive predictive values (prediction of significant fibrosis) or negative predictive values, the number of biopsy indications could be reduced. This could be useful for patients and society in order to reduce the cost and the risk of biopsies especially liver biopsies (6).

DESCRIPTION OF THE FIGURES

FIG. 4a: 6 markers function F0 n=56 median=0.10; F1 n=145 median=0.22; F2 n=68 median=0.41; F3 n=28 median=0.66; F4 n=42 median=0.89.

FIG. 4b: 5 markers function F0 n=55 median=0.14; F1 n=139 median=0.21; F2 n=64 median=0.43; F3 n=26 median=0.73; F4 n=41 median=0.85. The top and bottom of the box are the 25th and 75th percentiles. The length of the box is thus the interquartile range. That is, the box represents the middle 50% of the data. A line is drawn through the middle of the box at the median (the 50th percentile). The upper adjacent value is the largest observation that is less than or equal to the 75th percentile plus 1.5 times interquartile range. The lower adjacent value is the smallest observation that is greater than or equal to the 25th percentile minus 1.5 times interquartile range. Analysis of variance shows significant differences between all stages.(Bonferroni all-pairwise Multiple Comparison Test; p<0.001).

FIG. 5a: For Alpha 2 Globulins values, the only significant differences were between stage 4 versus stage 1 and stage 3.(Bonferroni all-pairwise Multiple Comparison Test; p=0.01).

FIG. 5b: For Alpha 2 Macroglobulin, there was a significant difference between stage 0 and 1 values lower than stages 2,3 and 4. (Bonferroni all-pairwise Multiple Comparison Test; p<0.001). Values of stage 2 were lower than values of stage 3 and 4.(Bonferroni all-pairwise Multiple Comparison Test; p<0.001). There was no significant difference between stage 0 and 1 and between stage 3 and 4.

FIG. 5c: For Haptoglobin there was a significant difference between stage 1 values higher than stages 2,3 and 4. (Bonferroni all-pairwise Multiple Comparison Test; p<0.001). Values of stage 4 were lower than values of stage 0,1 and 2.(Bonferroni all-pairwise Multiple Comparison Test; p<0.001). There was no significant difference between stage 0 and 1 and between stage 3 and 4.

DESCRIPTION OF THE PREFERRED EMBODIMENTS

The present invention is therefore drawn to a method for diagnosis of an inflammatory, a fibrotic or a cancerous disease in a patient comprising the steps of:
a) measuring the values of biochemical markers in the serum of said patient,
b) combining said values through a logistic function including said markers and,
c) analyzing the end value of said logistic function in order to determine the presence of liver fibrosis and/or liver necroinflammatory lesions in said patient.

The biochemical markers can also been assessed in the plasma of the patients, and the method can be considered as in vitro, when an optional first step (harvesting serum or plasma of patients) is not used.

In particular, the method of the invention is perfectly suited for diagnosis of liver fibrosis and/or presence of liver necroinflammatory lesions in said patient. It can also be performed for diagnosis of inflammatory and/or fibrotic disease in the lungs or kidneys of patients. It is also suited for the diagnosis of cancerous lesions, for example in lungs, breasts, bladder, colon.

The logistic function may be obtained through the following method:
i) classification of the patients in different groups according to the extend of their disease;
ii) identification of factors which differ significantly between these groups by unidimensional analysis;
iii) logistic regression analysis to assess the independent discriminative value of markers for the diagnosis of fibrosis and/or liver necroinflammatory lesions
iv) construction of the logistic function by combination of these identified independent factors (construction of an index).

By definition the best index ("fibrosis score") in term of discrimination was the logistic regression function combining the independent factors.

The logistic function is obtained by combining the relative weight of each parameter, as individually determined in the logistic regression, with a negative sign when the markers harbor a negative correlation with the stage of fibrosis. Logarithms are used for markers whose values have a very large range.

The quality of the logistic function is analyzed with the aid of a ROC curve, that is obtained depending of the threshold desired for the diagnosis. The way of obtaining the ROC curve is described in the examples. In the present invention, the classification of the patients was the presence of fibrosis, starting at few septa, but it could be changed if diagnosis of patient only with a large number of septa or with cirrhosis was intended. This leads to another ROC curve, as discussed in the examples.

The diagnosis of the presence of liver fibrosis and/or liver necroinflammatory lesions in the patient can be further refined by the data concerning the to the expected prevalence of liver fibrosis in the population.

Preferably, the biochemical markers that are dosed in step a) of the method according to the present invention are "simple" biochemical markers, which means that they are easily dosed with methods already known in the art (chromatography, electrophoresis, ELISA dosing . . . ).

Thus, markers that are perfectly suitable for the method of the invention include α2-macroglobulin, alanine aminotransferase (ALT), aspartate aminotransferase (AST), gammaglutamyl transpeptidase (GGT), γ-globulin, total bilirubin, albumin, α1-globulin, α2-globulin, haptoglobin, β-globulin, apolipoproteinA1 (apoA1), IL10, TGF-β1, apoA2, apoB. Depending of the studied disease, on could also use other cytokines, or specific markers known by the person skilled in the art. For the analysis of kidney or bladder disease, it may be convenient to perform some hosing of urine samples on the patient.

In a particular embodiment of the method of the invention, at least 4, more preferably 5 or 6, 7 or 10 biochemical markers are studied and dosed in step a) of the method.

Preferably, these markers are α2-macroglobulin, GGT, γ-globulin, total bilirubin, (α2-globulin or haptoglobin) and apoA1, when diagnosis of liver fibrosis is intended. Haptoglobin can be used in place of α2-globulin, as α2-globulin is the sum of α2-macroglobulin and α2-microglobulins, which are mainly composed of haptoglobin. The relative weight of α2-microglobulin and haptoglobin would therefore be adjusted in the logistic function.

When diagnosis of the presence of liver necroinflammatory lesions is intended, it is best when the markers that are dosed include α2-macroglobulin, GGT, γ-globulin, (ALT or AST) and apoA1. AST or ALT can indifferently be used as the data reported in the present application shows that these markers are correlated. Therefore, replacement of one marker by the other only results in the balancing of the coefficient in the logistic function, taking the correlation factor into account.

The logistic function can also use other markers such as the age and gender of the patient. The different coefficients used for the values obtained for the different markers in the logistic function can be calculated through statistical analysis, as described in the examples.

In particular, suitable logistic functions that can be used for the implementation of the method of the invention are as follow:

Using six markers:

$f1 = a_1 \times \text{Log} [\alpha2\text{-macroglobulin (g/l)}] - a_2 \times [\alpha2\text{-globulin (g/l)}] + a_3 \times \text{Log} [\text{GGT (IU/l)}] + a_4 \times [\gamma\text{-globulin (g/l)}] + a_5 \times [\text{Age (years)}] + a_6 \times \text{Log} [\text{Bilirubin (umol/l)}] - a_7 \times [\text{ApoA1 (g/l)}] + a_8 \times [\text{Sex (female=0, male=1)}] - a_9$, with $a_1$ comprised between 6.5 and 6.9,
$a_2$ comprised between 0.450 and 0.485,
$a_3$ comprised between 1.100 and 1.300,
$a_4$ comprised between 0.0700 and 0.0750,
$a_5$ comprised between 0.0265 and 0.0300,
$a_6$ comprised between 1.400 and 1.700,
$a_7$ comprised between 0.900 and 1,
$a_8$ comprised between 0.300 and 0.450, and
$a_9$ comprised between 4.200 and 4.700.

Specific usable functions are in particular:

$f1\text{-}a = 6.826 \times \text{Log} [\alpha2\text{-macroglobulin (g/l)}] - 0.479 \times [\alpha2\text{-globulin (g/l)}] + 1.252 \times \text{Log} [\text{GGT (IU/l)}] + 0.0707 \times [\gamma\text{-globulin (g/l)}] + 0.0273 \times [\text{Age (years)}] + 1.628 \times \text{Log} [\text{Bilirubin (umol/l)}] - 0.925 \times [\text{ApoA1 (g/l)}] + 0.344 \times [\text{Sex (female=0, male=1)}] - 4.544;$ or $f1\text{-}b = 6.552 \times \text{Log} [\alpha2\text{-macroglobulin (g/l)}] - 0.458 \times [\alpha2\text{-globulin (g/l)}] + 1.113 \times \text{Log} [\text{GGT (IU/l)}] + 0.0740 \times [\gamma\text{-globulin (g/l)}] + 0.0295 \times [\text{Age (years)}] + 1.473 \times \text{Log} [\text{Bilirubin (umol/l)}] - 0.979 \times [\text{ApoA1 (g/l)}] + 0.414 \times [\text{Sex (female=0, male=1)}] - 4.305;$ Using 10 markers:

$$f2 = b_1 \times \text{Log }[\alpha\text{2-macroglobulin (g/l)}] - b_2 \times [\alpha\text{2-globulin (g/l)}] + b_3 \times \text{Log }[\text{GGT (IU/l)}] + b_4 \times [\gamma\text{-globulin (g/l)}] + b_5 \times [\text{Age (years)}] + b_6 \times \text{Log }[\text{Bilirubin (umol/l)}] - b_7 \times [\text{ApoA1 (g/l)}] + b_8 \times [\text{Sex (female=0, male=1)}] + b_9[\text{Albumin (g/l)}] + b_{10}[\alpha\text{1-globulin (g/l)}] - b_{11}[\beta\text{2-globulin (g/l)}]2.189 - b_{12} \times \text{Log }[\text{ALT (IU/l)}] - b_{13}, \text{ with}$$

$b_1$ comprised between 9.9 and 10.2,
$b_2$ comprised between 0.7 and 0.77,
$b_3$ comprised between 2 and 2.4,
$b_4$ comprised between 0.1 and 0.2,
$b_5$ comprised between 0.04 and 0.07,
$b_6$ comprised between 4 and 4.6,
$b_7$ comprised between 2 and 2.5,
$b_8$ comprised between 0.28 and 0.32
$b_9$ comprised between 0.025 and 0.04
$b_{10}$ comprised between 2 and 2.2
$b_{11}$ comprised between 0.1 and 0.16
$b_{12}$ comprised between 0.7 and 0.9, and
$b_{13}$ comprised between 12 and 14.

A specific usable function is in particular:

$$f2 = 10.088 \times \text{Log }[\alpha\text{2-macroglobulin (g/l)}] - 0.735 \times [\alpha\text{2-globulin (g/l)}] + 2.189 \times \text{Log }[\text{GGT (IU/l)}] + 0.137 \times [\gamma\text{-globulin (g/l)}] + 0.0546 \times [\text{Age (years)}] + 4.301 \times \text{Log }[\text{Bilirubin (umol/l)}] - 2.284 \times [\text{ApoA1 (g/l)}] + 0.294 \times [\text{Sex (female=0, male=1)}] + 0.0312 [\text{Albumin (g/l)}] + 2.109 [\alpha\text{1-globulin (g/l)}] - 0.136 [\beta\text{2-globulin (g/l)}] - 0.813 \times \text{Log }[\text{ALT (IU/l)}] - 13.165.$$

Using six markers to determine significant activity:

$$f3 = c_1 \times \text{Log }[\alpha\text{2-macroglobulin (g/l)}] - c_2 \times [\beta\text{2-globulin (g/l)}] + c_3 \times \text{Log }[\text{GGT (IU/l)}] + c_4 \times [\gamma\text{-globulin (g/l)}] - c_5 \times [\text{Age (years)}] + c_6 \times \text{Log }[\text{ALT (IU/l)}] - c_7 \times [\text{ApoA1 (g/l)}] - c_8 \times [\text{Sex (female=0, male=1)}] - c_9, \text{ with}$$

$c_1$ comprised between 3.45 and 3.65,
$c_2$ comprised between 0.3 and 0.4,
$c_3$ comprised between 0.8 and 1,
$c_4$ comprised between 0.075 and 0.09,
$c_5$ comprised between 0.0015 and 0.003,
$c_6$ comprised between 2.1 and 2.5,
$c_7$ comprised between 1.55 and 1.75,
$c_8$ comprised between 0.35 and 0.45, and
$c_9$ comprised between 4 and 4.6.

A specific usable function is notably:

$$f3 = 3.513 \times \text{Log }[\alpha\text{2-macroglobulin (g/l)}] - 0.354 \times [\beta\text{2-globulin (g/l)}] + 0.889 \times \text{Log }[\text{GGT (IU/l)}] + 0.0827 \times [\gamma\text{-globulin (g/l)}] - 0.0022 \times [\text{Age (years)}] + 2.295 \times \text{Log }[\text{ALT (IU/l)}] - 1.670 \times [\text{ApoA1 (g/l)}] - 0.415 \times [\text{Sex (female=0, male=1)}] - 4.311.$$

Using seven markers, for the diagnostic of significant fibrosis or significant activity:

$$f4 = d_1 \times \text{Log }[\beta\text{2-macroglobulin (g/l)}] - d_2 \times [\beta\text{2-globulin (g/l)}] + d_3 \times \text{Log }[\text{GGT (IU/l)}] + d_4 \times [\gamma\text{-globulin (g/l)}] + d_5 \times [\text{Age (years)}] + d_6 \times \text{Log }[\text{Bilirubin (umol/l)}] - d_7 \times [\text{ApoA1 (g/l)}] + d_8 \times [\text{Sex (female=0, male=1) }] + d_9 \text{Log }[\text{ALT (IU/l)}] - d_{10}, \text{ with}$$

$d_1$ comprised between 5.3 and 6.7,
$d_2$ comprised between 0.45 and 0.5,
$d_3$ comprised between 0.8 and 1.2,
$d_4$ comprised between 0.06 and 0.08,
$d_5$ comprised between 0.0015 and 0.0025,
$d_6$ comprised between 1 and 1.2,
$d_7$ comprised between 1 and 1.2,
$d_8$ comprised between 0.09 and 1.1,
$d_9$ comprised between 1.2 and 1.5, and
$d_{10}$ comprised between 4 and 5.

A specific usable function is:

$$f4 = 5.981 \times \text{Log }[\alpha\text{2-macroglobulin (g/l)}] - 0.481 \times [\alpha\text{2-globulin (g/l)}] + 0.965 \times \text{Log }[\text{GGT (IU/l)}] + 0.0679 \times [\gamma\text{-globulin (g/l)}] + 0.0190 \times [\text{Age (years)}] + 1.143 \times \text{Log }[\text{Bilirubin (umol/l)}] - 1.097 \times [\text{ApoA1 (g/l)}] + 0.092 \times [\text{Sex (female=0, male=1)}] + 1.355 \text{ Log }[\text{ALT (IU/l)}] - 4.498.$$

Using five markers, for the diagnosis of significant fibrosis:

$$f5 = z_1 \times \text{Log }[\alpha\text{2-macroglobulin (g/l)}] - z_2 \times \text{Log }[\text{Haptoglobin (g/l)}] + z_3 \times \text{Log }[\text{GGT (IU/l)}] + z_4 \times [\text{Age (in years)}] + z_5 \times \text{Log }[\text{Bilirubin (umol/l)}] - z_6 \times [\text{ApoA1 (g/l)}] + z_7 \times \text{Sex (female=0, male=1)} - z_8, \text{ with}$$

$z_1$ comprised between 4 and 5,
$z_2$ comprised between 1.2 and 1.5,
$z_3$ comprised between 0.9 and 1.1,
$z_4$ comprised between 0.0026 and 0.03,
$z_5$ comprised between 1.6 and 1.9,
$z_6$ comprised between 1 and 1.3,
$z_7$ comprised between 0.25 and 0.35, and
$z_8$ comprised between 5 and 6.

A specific usable function is:

$$f5 = 4.467 \times \text{Log }[\alpha\text{2-macroglobulin (g/l)}] - 1.357 \times \text{Log }[\text{Haptoglobin (g/l)}] + 1.017 \times \text{Log }[\text{GGT (IU/l)}] + 0.0281 \times [\text{Age in years}] + 1.737 \times \text{Log }[\text{Bilirubin (umol/l)}] - 1.184 \times [\text{ApoA1 (g/l)}] + 0.301 \times \text{Sex (female=0, male=1)} - 5.540.$$

In fact, the numerical definitions for the coefficients in the different functions can slightly vary (about 10–15%) depending of the number and characteristics of patients studied. Therefore, the value given for the coefficients of the different markers have to be interpreted as capable to being slightly different, without reducing the scope of the invention.

Depending of the end value obtained by the analysis with the logistic function of the value measured for the biological markers, it is possible to draw conclusions about the presence of liver fibrosis for the patient. It is also possible to conclude about the presence of cirrhosis, by taking cirrhosis as the threshold in the drawing of the ROC curve.

The method of the invention is also usable as a predictive mean for the evolution of the disease. In particular, when the patient is infected with the hepatitis C virus, it is often possible to determine the date of the infection (usually through transfusion). Therefore, the use of the method of the invention to determine the degree of evolution of the disease through the date of the diagnosis can also allow for the prognosis of the future development of the disease.

The data obtained by the diagnosis method according to the invention can also be very valuable for the physician to chose a suitable treatment for the patient, according to the stage of the disease.

Depending of the prevalence of liver fibrosis in the population of patients that are consulting, the data obtained with the method of the invention can be used to determine the need to perform a liver biopsy on the patient. It is expected that the method of the invention will reduce the need of liver biopsy by around 50%.

The method of the invention is intended to be used for patient suffering of any disease involving liver fibrosis, that could develop to cirrhosis. In particular, the method of the invention is advantageously performed for detecting liver fibrosis in patient suffering form a disease included in the group consisting of hepatitis B and C, alcoholism, hemochromatosis, metabolic disease, diabetes, obesity, autoimmune hepatitis, primary biliary cirrhosis, α1-antitrypsin deficit, Wilson disease.

The method of the invention is best performed on patients infected with a hepatitis virus, in particular the hepatitis C virus.

The invention is also drawn to a kit of diagnosis of an inflammatory, a fibrotic or a cancerous disease in a patient, comprising instructions allowing to determine the presence of said inflammatory, fibrotic or cancerous disease in said patient, after the dosage of biochemical markers.

The invention is also drawn to a kit of diagnosis of liver fibrosis and/or liver necroinflammatory lesions in a patient, comprising instructions allowing to determine the presence of liver fibrosis and/or liver necroinflammatory lesions in said patient, after dosage of biochemical markers.

The instructions may comprise the logistic function that has to be use after determination of the dosage of the biochemical markers. It can appear as a printed support as well as a computer usable support, such as a software. The instructions may also comprise the ROC curve depending of the threshold that is looked for, to allow the analysis of the end data obtained from the logistic function. They may also comprise different tables that allow to obtain the predictive values, depending of the expected prevalence of fibrosis in the patient population.

The diagnosis kit according to the present invention may also contain elements allowing the dosage of the biological markers of interest.

The method of the invention can easily be automated, the dosage of the markers being performed automatically, the data being sent to a computer or a calculator that will calculate the value of the logistic function and analyze it with the aid of the ROC curve, and eventually the prevalence of liver fibrosis in the patient population. The data obtained by the physician is therefore more easily interpretable, and will allow for an improvement in the process for deciding the need of a biopsy or the adequate treatment to prescribe.

The following examples are meant to describe an aspect of invention, and give the methodology in order to repeat the method of the invention, but shall not be limiting the invention.

EXAMPLES

Example 1

Patients and Methods 1.1. Patients

Patients included in the study belonged to a single center cohort, named Hepatite C Pitie-Salpetriere, (DOSVIRC). This cohort included all the patients with hepatitis C (defined as a positive serology by at least a second generation ELISA test) followed in the liver and gastrointestinal unit of Pitie-Salpetriere Hospital, Paris, France, retrospectively before 1993 and prospectively afterwards (16). A specific questionnaire was filled out for each patient which contained 129 items including social-demographic-administrative data, risk factors, and at each visit clinical, biologic, virologic and treatment items, and histologic data when liver biopsy was performed. The duration of HCV infection was estimated from the date of transfusion or initial exposure to other parenteral sources, and it could not be calculated for patients with sporadic infection or those in whom the source of infection was unknown. Exclusion criteria were the presence of HBsAg or HIV positive antibodies. From August 1997 to March 2000 all informed patients with detectable HCV by PCR undergoing a liver biopsy were pre-included and a blood sample taken the day of biopsy. Exclusion criteria were coinfection with HIV, HBV other liver disease, and non interpretable liver biopsy.

The analysis was performed on a first period (first year training period 206 patients) and validated on the second period (validation period 156 patients) (Table 1)

Another analysis was performed after exclusion of one patient in the training period, and 22 patients in the validation period (Table 4).

1.2. Serum Markers

The 11 following tests were assessed for the 2 periods: alpha2-macroglobulin, AST, ALT, GGT, total bilirubin, albumin, alpha1 alpha2 beta and gamma globulins, apo A1. To explain the independent diagnostic value of alpha2 globulins (mainly made up of alpha2-macroglobulin and haptoglobin), a retrospective assessment of haptoglobin was performed on the 2 periods.

IL10, TGF-β1, apoA2 and apoB were assessed for the second period only.

AST, ALT, GGT, total bilirubin, were assessed by Hitachi 917 automate using Roche Diagnostics reagents (Mannheim Germany).

Albumin was assessed by bromocresol green method (17) independently of serum proteins electrophoresis, (alpha1, alpha2, beta and gamma globulins fractions) which were conducted in an automatic system Hydrasys and Hyrys (Sebia, Issy-Les-Moulineaux, France).

Apolipoproteins A1, -A2, -B and alpha2macroglobulin were determined in serum samples (preserved at −80° C. until assay) by using an automatic nephelometer BNII (Dade Behring Marburg, Germany).

Plasma TGFbeta1 concentration was measured using Quantikine human TGFbeta1 immunoassay (R and D Systems, Inc. Minneapolis, Minn., USA). To activate latent TGFbeta1 to the immunoreactive form, the samples were activated by acid and neutralized thereafter.

Plasma Interleukin 10 were measured using an immunoassay kit (Beckman Coulter Company Immunotech, Marseille, France).

Plasmas samples were preserved at −80° C. until assay (less than one year).

1.3. Histological Staging and Grading

Histological features of liver specimens were analyzed according to the METAVIR scoring system (18,19). Liver biopsies, more than 10 mm in length, were fixed, paraffin-embedded and stained with at least hematoxylin eosin safran and Masson's trichrome or picrosirius red for collagen.

For each liver biopsy, a stage of fibrosis and a grade of activity was established according to the following criteria. Liver biopsy was staged on a scale of 0 to 4:0 =no fibrosis, 1=portal fibrosis without septa, 2=few septa, 3=numerous septa without cirrhosis, and 4=cirrhosis. This feature has been shown to be highly reproducible between pathologists.

The grading of activity that evaluates the intensity of necroinflammatory lesions was indicated as follows: A0=no histological activity, A1=mild activity, A2=moderate activity, and A3=severe activity. The METAVIR scoring system was assessed by a single pathologist (FC) unaware of patients characteristics.

Example 2

Statistical Analysis

Statistical analysis used logistic regression and ROC curves (20). The analysis was performed on a first period (first year training period) and validated on the second period (validation period), cohort of patients as in Tables 1 and 4.

Then a final analysis was performed on the overall population combining the two periods (see tables 2 and 5).

According to the METAVIR scoring system, patients were divided into several groups.

The major endpoint was the identification of patients with significant fibrosis (F2, F3 or F4) versus patients without significant fibrosis (F0 or F1).

In secondary analyses patients were also divided according to activity grades: patients without significant activity (A0 or A1) and patients with histological activity (A2, or A3).

A group with non-significant histological features (A<2 and F<2) and a group of significant lesions (A$\geq$2 and/or F$\geq$2) were defined.

Finally a group with extensive fibrosis or cirrhosis (F3 or F4) was also defined.

The first stage consisted of identifying factors which differed significantly between these groups by unidimensional analysis using the chi-square, Student t test or Mann-Whitney test.

The second stage consisted of logistic regression analysis to assess the independent discriminative value of markers for the diagnosis of fibrosis.

The third step was to construct an index combining these identified independent factors. By definition the best index ("fibrosis score") in term of discrimination was the logistic regression function combining the independent factors.

The diagnostic values of these indexes and of the isolated factors were assessed by sensitivity, specificity, positive and negative predictive values and receiver operating characteristics. The predictive values were assessed for the observed prevalence of significant fibrosis (40% in this study), but also for lower (10%) or higher prevalence (90%).

The respective overall diagnostic values were compared by the area under the Receiver Operating Characteristic curves. The ROC curve is drawn by plotting the sensitivity versus (1-specificity), after classification of the patients, according to the value obtained for the logistic function, for different thresholds (from 0 to 1). It is usually acknowledged that a RCO curve the area under which has a value superior to 0.7 is a good predictive curve for diagnosis. The ROC curve has to be acknowledged as a curve allowing to predict the quality of a diagnosis method.

These statistical analyses were performed separately for the different groups, as previously defined.

In order to reduce the number of factors, an analysis combining only the 6 most significant markers was performed (f1-a, or f1-b).

Since it was observed, during the analyses, that alpha 2 globulins had an independent diagnostic value when alpha 2 macroglobulin was taken into account, the diagnostic value of haptoglobin, the second main component of alpha 2 globulins, was retrospectively assessed.

An index with five markers, excluding protein electrophoresis components, was finally constructed combining haptoglobin and the four other identified markers (logistic function f5).

Example 3

Determination of the Logistic Function

A total of 422 patients with chronic hepatitis C were pre-included.

Depending of the number excluded for the following reasons (HIV coinfection, HBV coinfection and transplantation), of the impossibility of fibrosis staging was impossible in others, or the impossibility of dosage of at least one out of the 11 markers, total of 362 ($1^{st}$ study) or 339 ($2^{nd}$ study) patients with chronic hepatitis C were included in the study, as indicated in Tables 1 and 4, respectively.

There was no difference between the patients characteristics and biochemical markers between first and second sample (Tables 1 and 4). The overall prevalence of significant fibrosis was 40% (F0 17–18%, F1 42–43%, F2 19–20%, F3 8%, F4 12–13%), as determined by histology.

3.1. Diagnosis of Significant Fibrosis

The diagnostic values (area under the ROC curves) of each of the eleven biochemical markers are given in tables 2 and 5 as well as their independent association with fibrosis (logistic regression).

The fibrosis score combining the ten or the six most informative markers (alpha2-macroglobulin, alpha2-microglobulin, total bilirubin, gamma globulin, apo A1, and GGT) or five markers (after excluding alpha2-microglobulin, gamma globulin and including haptoglobin), and age and gender had high diagnostics values, on the training sample as well as on the validation sample and in the overall population (Table 2 and 5).

Because transaminases ALT and AST were highly correlated (correlation coefficient=0.88) only ALT was used, when this marker was needed.

The logistic function of 6 markers and age and sex was determined to be as follow:

$f1\text{-}a = 6.826 \times \text{Log}\ [\alpha2\text{-macroglobulin (g/l)}] - 0.479 \times [\alpha2\text{-globulin (g/l)}] + 1.252 \times \text{Log}\ [\text{GGT (IU/l)}] + 0.0707 \times [\gamma\text{-globulin (g/l)}] + 0.0273 \times [\text{Age (years)}] + 1.628 \times \text{Log}\ [\text{Bilirubin (umol/l)}] - 0.925 \times [\text{ApoA1 (g/l)}] + 0.344 \times [\text{Sex (female=0, male=1)}] - 4.544;$ or $f1\text{-}b = 6.552 \times \text{Log}\ [\alpha2\text{-macroglobulin (g/l)}] - 0.458 \times [\alpha2\text{-globulin (g/l)}] + 1.113 \times \text{Log}\ [\text{GGT (IU/l)}] + 0.0740 \times [\gamma\text{-globulin (g/l)}] + 0.0295 \times [\text{Age (years)}] + 1.473 \times \text{Log}\ [\text{Bilirubin (umol/l)}] - 0.979 \times [\text{ApoA1(g/l)}] + 0.414 \times [\text{Sex (female=0, male=1)}] - 4.305;$ The logistic function of 6 markers and age and sex was determined to be as follow:

$f5 = 4.467 \times \text{Log}\ [\alpha2\text{-macroglobulin (g/l)}] - 1.357 \times \text{Log}\ [\text{Haptoglobin (g/l)}] + 1.017 \times \text{Log}\ [\text{GGT (IU/l)}] + 0.0281 \times [\text{Age (in years)}] + 1.737 \times \text{Log}\ [\text{Bilirubin (umol/l)}] - 1.184 \times [\text{ApoA1 (g/l)}] + 0.301 \times \text{Sex (female=0, male=1)} - 5.540.$ These functions were obtained by combining the relative weight of each parameter, as individually determined in the logistic regression, with a negative sign when the markers harbors a negative correlation with the stage of fibrosis. Logarithms were used for markers whose values have a very large range.

Figure 1:
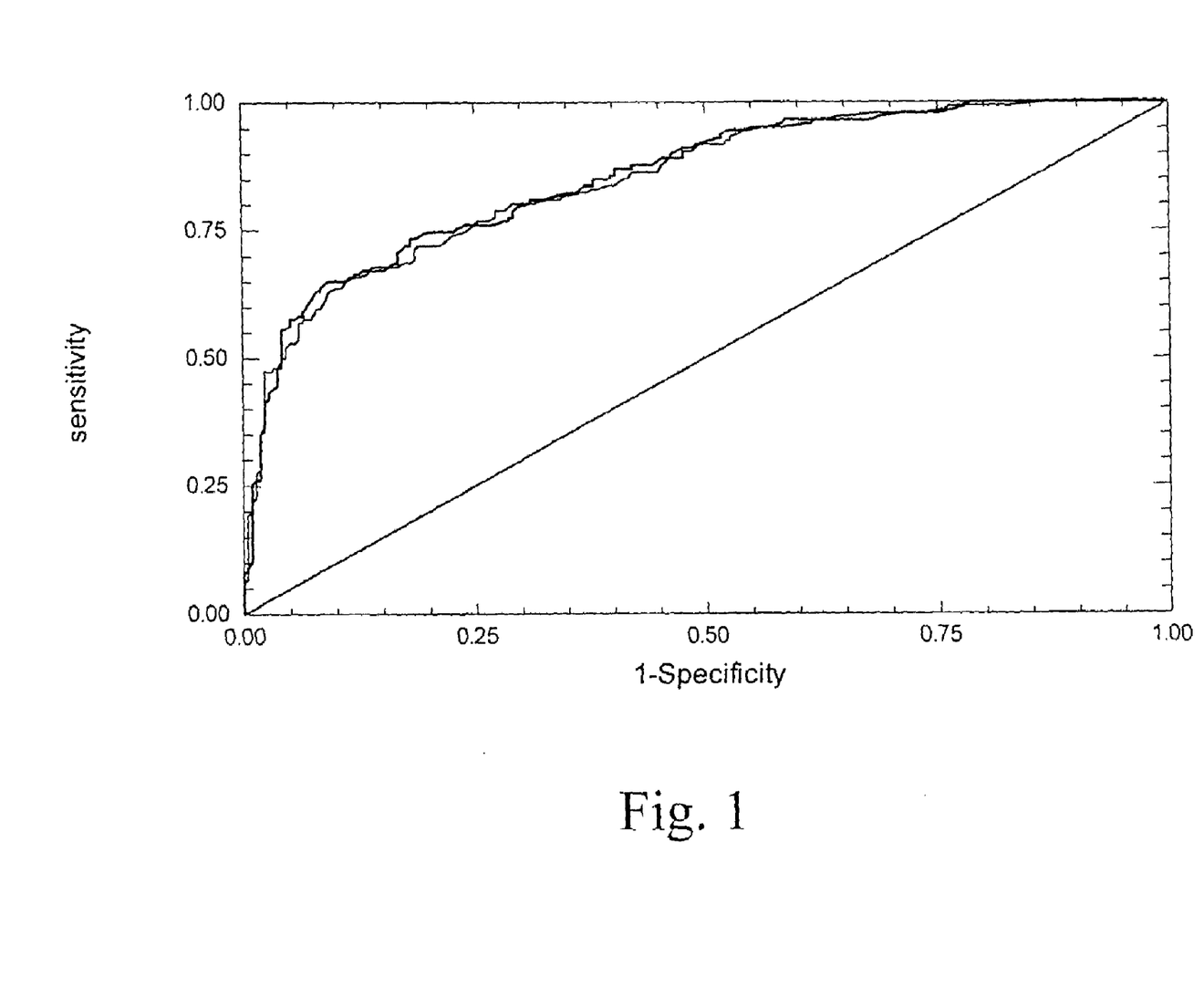
FIG. 1: Receiver Operating Characteristic (ROC) curves of the fibrosis markers function combining six (alpha2-macroglobulin, alpha2-microglobulin, total bilirubin, gamma globulin, apo A1, and GGT,) or ten biochemical factors (same plus albumin, alpha1-microglobulin, beta globulin and ALT,) and the age and gender. The area under the curve were not different: 0.853±0.02 and 0.851±0.02 respectively.
Figure 3:
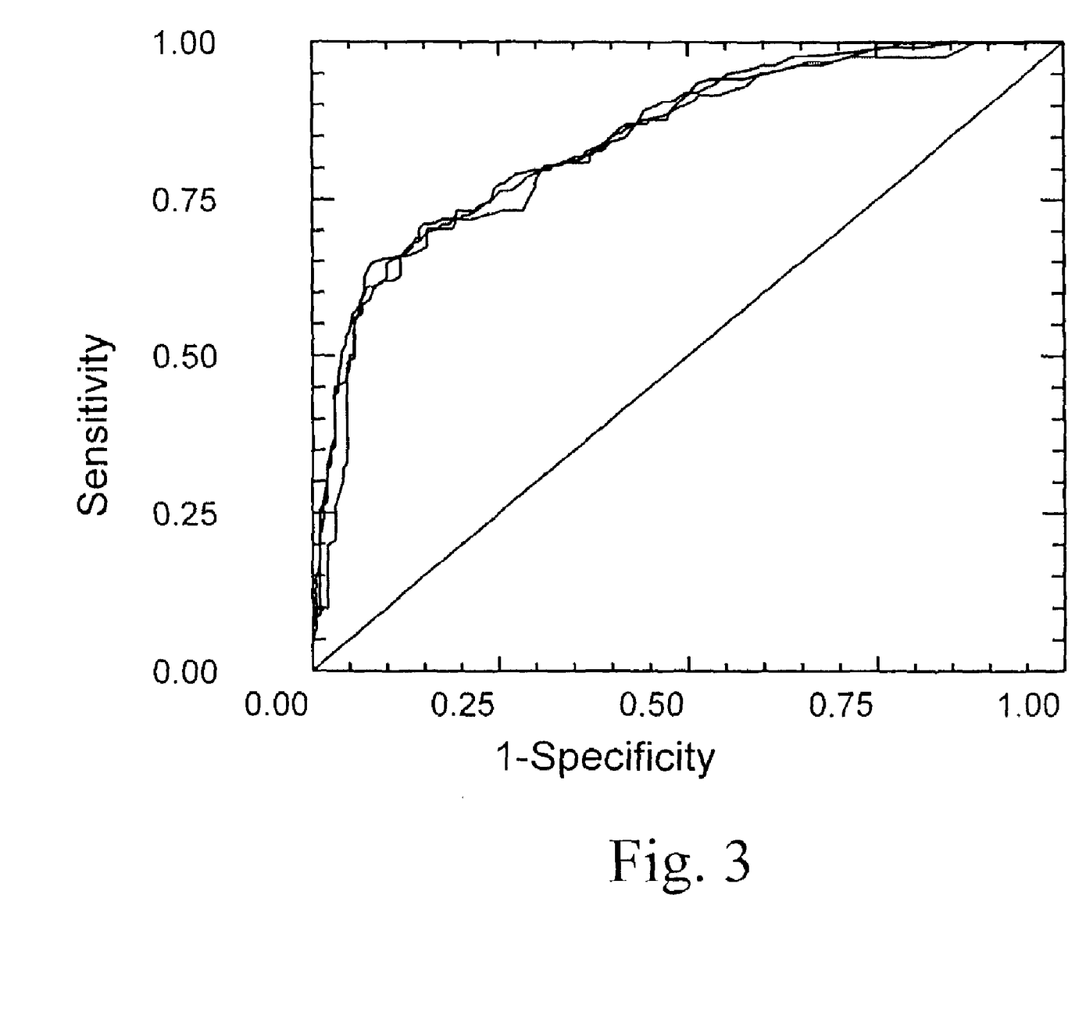
FIG. 3: ROC curves of the fibrosis markers function combining five (Alpha2-Macroglobulin, Haptoglobin, total Bilirubin, Apo A1, and GGT), six (alpha2-macroglobulin, alpha2-microglobulin, total bilirubin, gamma globulin, apo A1, and GGT) or ten biochemical factors (same plus albumin, alpha1-microglobulin, beta globulin and ALT,) and the age and gender. The area under the curve were not significantly different: 0.837±0.02, 0.847±0.02 and 0.851±0.02 respectively.

When 10 markers were used for the calculation of the logistic function for the determination of fibrosis, the function was as follow:

$f2 = 10.088 \times \text{Log} [\alpha2\text{-macroglobulin (g/l)}] - 0.735 \times [\alpha2\text{-globulin (g/l)}] + 2.189 \times \text{Log} [\text{GGT (IU/l)}] + 0.137 \times [\gamma\text{-globulin (g/l)}] + 0.0546 \times [\text{Age (years)}] + 4.301 \times \text{Log} [\text{Bilirubin (umol/l)}] - 2.284 \times [\text{ApoA1 (g/l)}] + 0.294 \times [\text{Sex (female=0, male=1)}] + 0.0312 [\text{Albumin (g/l)}] + 2.109 [\alpha1\text{-globulin (g/l)}] - 0.136 [\beta2\text{-globulin (g/l)}] - 0.813 \times \text{Log} [\text{ALT (IU/l)}] - 13.165;$ The ROC curves for the fibrosis score using the ten or the six most informative markers (FIG. 1), or the ten, six or five most informative markers (FIG. 3) were identical. The area under the curve were not different.

Figure 2:
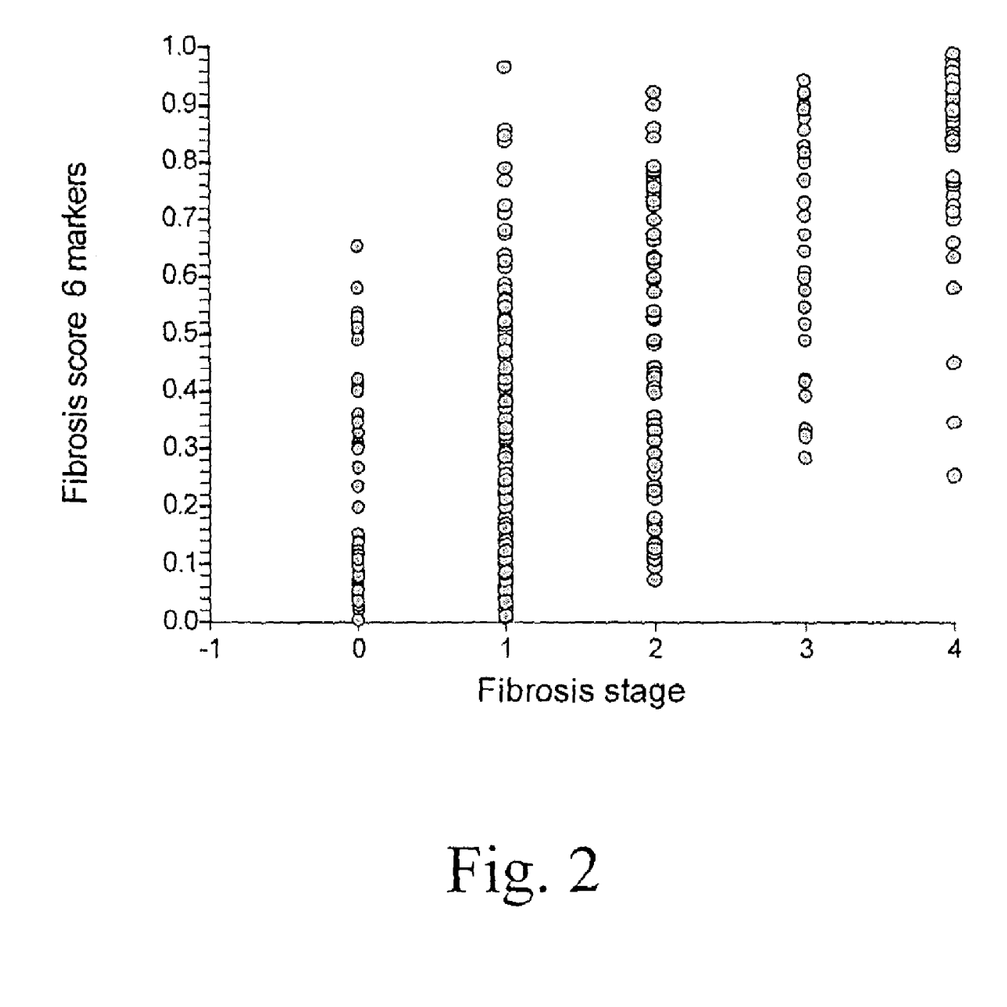
FIG. 2: scatter plot of the six markers fibrosis score (ranging from 0.00 to 1.00), according to fibrosis stage.

The scatter plot of the six markers fibrosis score (which ranges from 0.00 to 1.00), according to fibrosis stage is given in FIG. 2.

Figure 4:
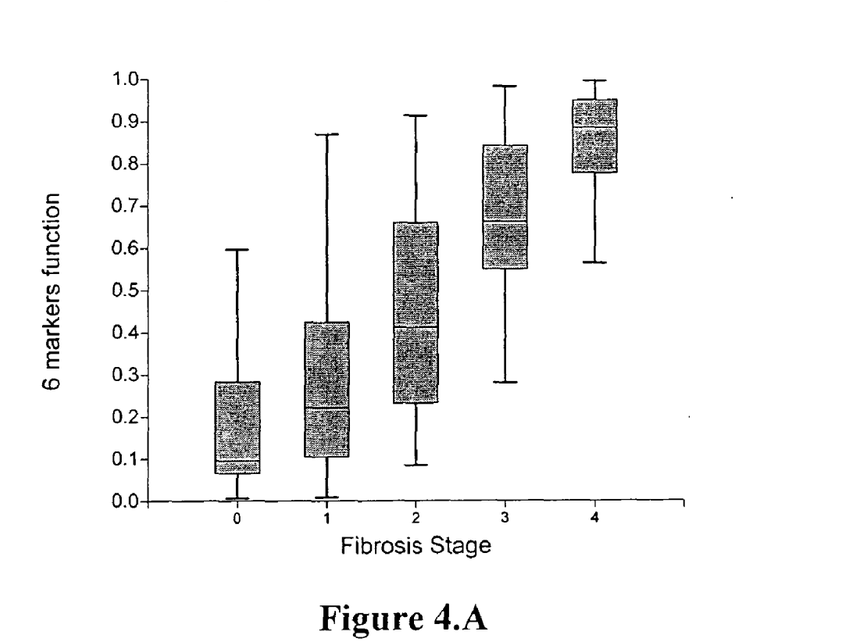
FIG. 4: Fibrosis Score according to fibrosis stage

The box plots of the five or six markers fibrosis score (which ranges from 0.00 to 1.00), according to fibrosis stage, are given in FIG. 4.

Using the six markers fibrosis score, high negative predictive value (>90% absence of F2 F3 F4) was obtained for score ranging from 0 to 0.20 (125 patients ($1^{st}$ study), or 119 patients ($2^{nd}$ study)), that is about 35% of patients, with 13 false negative aged from 34 to 59 years: 4 F2A0, 6 F2A1, 3F2A2). High positive predictive value (>90% presence of F2 F3 F4) was obtained for score from 0.80 to 1 (53 patients ($1^{st}$ study), resp. 50 patients ($2^{nd}$ study), that is 15% of patients, with 4, resp. 5, false positive aged from 47 to 68 years: 1, reps.2, F1A1, 3 F1A2) (Tables 3 and 6).

These value were calculated for a prevalence of fibrosis (F>1) of 40% in the test population. The values for prediction that are to be considered if the prevalence of fibrosis in the test population is 90% or 10% are also indicated in Tables 3 and 6.

Neural connection methods gave similar results : the percentage of patients correctly classified was 77%, 74% and 79% for the training, validation and test samples, respectively (not shown).

In the second sample the addition of IL10, TGFB1, apoA2 and apoB permitted to slightly increase the area curve to 0.889±0.030, not different from the 6 markers fibrosis score.

3.2. Diagnosis of Significant Fibrosis Among Patients with Low ALT ($2^{nd}$ Study)

A total of 43 patients had ALT lower than 35 IU/l , with 10 patients having significant fibrosis. The diagnostic value of the 6 markers fibrosis function was still high with the area under the ROC curve 0.758±0.090. The two patients with a score greater than 0.80 had a cirrhosis. Among 29 patients with scores lower than 0.20, 25 had no significant fibrosis.

3.3. Diagnosis of Cirrhosis or Extensive Fibrosis ($1^{st}$ Study)

For the diagnosis of cirrhosis or extensive fibrosis, a fibrosis score using the same 6 markers ($R^2=0.345$ P<0.001) reached a very high area under the ROC curve: 0.929±0.020.

Using this function, high negative predictive value (>90% absence of F3 F4) was obtained for score ranging from 0 to 0.80 (309 patients, that is 85% of patients, with 32 false negative aged from 27 to 74 years: 13 cirrhosis and 19 F3). For score >0.80 there was a high positive predictive value (>85% presence of F3 F4) 53 patients, that is 15% of patients, with 8 false positive aged from 47 to 68 years: 4 F2 and 2 F1.

3.4. Diagnosis of Cirrhosis or Extensive Fibrosis ($2^{nd}$ Study)

For the diagnosis of cirrhosis or extensive fibrosis, the same fibrosis score using 6 markers ($R^2=0.347$; p<0.001) reached a very high area under the ROC curve: 0.923±0.020.

Using this function, a high negative predictive value (>90% absence of F3 F4) was obtained for scores ranging from 0 to 0.80. Out of these 289 patients, being 85% of the total, there were 30 false negatives: 11 cirrhosis and 19 F3. For scores >0.80, there was a high positive predictive value (>85% presence of F3 F4). Out of these 50 patients, that is 15% of the total, there were 10 false positives: 5 F2 and 5 F1.

3.5. Diagnosis of Significant Activity or either Fibrosis or Activity ($1^{st}$ and $2^{nd}$ Study)

For the diagnostic of significant activity (A2A3) the best final logistic regression combined ALT, alpha2-macroglobulin, beta-globulin, gamma globulin, apo A1, and GGT ($R^2=0.243$ P<0.001).

The logistic function that was used was:

$f3 = 3.513 \times \text{Log} [\alpha2\text{-macroglobulin (g/l)}] 0.354 \times [\beta2\text{-globulin (g/l) (g/l)}] + 0.889 \times \text{Log} [\text{GGT (IU/l)}] + 0.0827 \times [\gamma\text{-globulin (g/l)}] - 0.0022 \times [\text{Age (years)}] + 2.295 \times \text{Log} [\text{ALT (IU/l)}] 1.670 \times [\text{ApoA1 (g/l)}] 0.415 \times [\text{Sex (female=0, male=1)}] 4.311;$ For the diagnostic of significant fibrosis (F2F3F4) or significant activity (A2A3) the best final logistic regression combined the same six markers as for significant fibrosis alone plus ALT ($R^2=0.290$ P<0.001).

The logistic function that one should use for this diagnostic reads:

$f4 = 5.981 \times \text{Log} [\alpha2\text{-macroglobulin (g/l)}] - 0.481 \times [\alpha2\text{-globulin (g/l)}] + 0.965 \times \text{Log} [\text{GGT (IU/l)}] + 0.0679 \times [\gamma\text{-globulin (g/l)}] + 0.0190 \times [\text{Age (years)}] + 1.143 \times \text{Log} [\text{Bilirubin (umol/l)}] - 1.097 \times [\text{ApoA1 (g/l)}] + 0.092 \times [\text{Sex (female=0, male=1)}] + 1.355 \text{ Log} [\text{ALT (IU/l)}] - 4.498.$ 3.6. Associations Between Cytokines and Biochemical Markers ($2^{nd}$ Study)

TGF-beta1 was positively associated with haptoglobin (R=0.39; p<0.001) and negatively with alpha2 macroglobulin (R=0.20; p=0.02), bilirubin (R=−0.32; p<0.001) and GGT (R=−0.20;p=0.01). HGF was associated with alpha2 macroglobulin (R=0.45; p=0.006) and GGT (R=0.54; p<0.001). IL10 was only associated with gamma-globulins (R=0.20; p=0.01).

Example 4

Analysis of the Data

The results obtained show that a combination of five or six simple biochemical markers, not directly related to fibrogenesis, can reach high positive or negative predictive values for the diagnosis of significant fibrosis even at the early stage of few septa.

Conclusions for diagnosis methods are usually weak if the studied sample is biased and not representative of the most common patients. The clinical, histological and biochemical characteristics of the prospective population in this study was stable during the 33 months of the study, and similar to populations included in recent large randomized trials (22). Patients with obvious decompensated cirrhosis were not included. Inclusion of patients with severe liver disease would have improved artificially the predictive values of the logistic function. On the other hand, there was also a significant number of patients with minimal histologic features (13–18% without fibrosis), and 9% of patients with ALT lower than 30 IU/ml, and 13% with ALT lower than 35 IU/ml, who are usually not included in randomized trials.

The diagnostic value of the fibrosis score was reproducible between the two periods (Tables 2 and 5). Analysis of these results allows the conclusion that the number of biopsy could be reduced by 50% in the management of chronic hepatitis C.

In practice, patients are treated according to fibrosis stage and grade (1–4). If a non-treatment decision without biopsy would have been taken according to a fibrosis score <0.20, only 13 out 125 or 119 patients were false negative. Among them none had cirrhosis or extensive fibrosis (F3–F4) and only two had moderate activity. If a treatment decision without biopsy would have been taken according to a fibrosis score >0.80, only 4 patients out of 53 or 5 out of 50, were false positive. Among them 3 patients had moderate activity which justified treatment despite only portal fibrosis according to consensus statement (2).

Two of these 3 patients underwent a transvenous liver biopsy showing elevated porto-caval gradient, 19 and 13 mmHg respectively. It is therefore highly possible that these patients had, in fact, a significant fibrosis.

In this instance, only one or two patients (4%) would have been treated in excess. Therefore, this score can also detect most patients with moderate and severe histological activity but without significant fibrosis. Finally, the fibrosis score could also be used for cirrhosis management without biopsy.

It is very important to notice that the method of the invention does not lead to a large number of undue treatment of patients or to the exclusion of patients in need of a treatment. The data presented in this application does strengthen the reliability of the method of diagnosis according to the present invention.

The fibrosis score could also be used for cirrhosis management without biopsy. Thus, screening for varices and for hepato-cellular carcinoma could be recommended in patients with fibrosis score >0.80.

The most informative markers were in decreasing rank: alpha2-macroglobulin, alpha2-globulin, GGT, gamma globulin, total bilirubin and apoA1.

Figure 5:
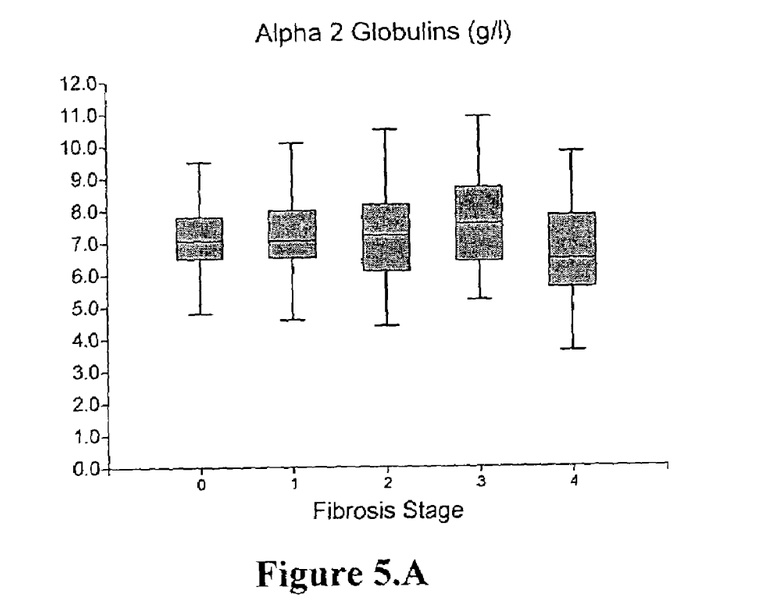
FIG. 5 : Alpha 2 Globulins, Alpha 2 Macroglobulin and Haptoglobin according to fibrosis stage.

Alpha2-globulin (normal range 4–6 g/l) is constitued by alpha2-macroglobulin (1.4–4.0 g/l), and alpha2-microglobulins: haptoglobin (0.4–2 g/l), caeruleoplasmin (0.2–0.4), antithrombin III (0.2–0.3) and retinol binding protein (0.03–0.07) (23). The diagnostic value of alpha2-globulin was not observed in univariate analysis because fibrosis was associated with an increase of alpha2-macroglobulin and a decrease of alpha2-microglobulins (FIG. 5).

The data reported suggests that haptoglobin, the main component of alpha2-microglobulins, decreased when fibrosis increased and is the predictive factor. Indeed, the difference between alpha2-globulin and alpha2-macroglobulin, mainly constituted by haptoglobin, was strongly and negatively associated with fibrosis (R=−0.33, p<0.001). The other components of alpha2-microglobulin (caeruleoplasmin, antithrombin III, and retinol binding protein) are in much lower serum concentration and their individual diagnostic value have not been assessed.

An opposite correlation could be observed between fibrosis and alpha2 macroglobulin (positively correlated R=0.46 p<0.001) versus alpha2 microglobulins (rich in haptoglobin, negatively correlated R=−0.40).

The logistic function with 5 markers strengthens this hypothesis.

A significant diagnostic value of increased alpha2-macroglobulin for fibrosis staging had already been observed in patients with alcoholic liver disease. Alpha2-macroglobulin belongs to the acute phase proteins and is produced locally by hepatocytes, stellate cells and granuloma cells at sites of inflammation and liver fibrosis. Moreover, alpha2-macroglobulin is specifically related to fibrosis as a feature of stellate cell activation. Alpha2-macroglobulin is also a proteinase inhibitor and an increased synthesis of it can inhibit the catabolism of matrix proteins and enhance fibrotic processes in the liver.

Haptoglobin decreases when fibrosis increases and thus explains the predictive value of alpha2-globulins when combined with alpha2-macroglobulins. Haptoglobin was strongly and negatively associated with fibrosis, as already observed. This association was not related to hemolysis, hypersplenism, or hepatic insufficiency. Similarly, no significant association with unconjugated bilirubin was found in this study (data not shown).

The opposite correlations with fibrosis between alpha2 macroglobulin (positive) and haptoglobin (negative) could be explained by the different roles of HGF and TGF-beta1 during fibrogenesis and the acute phase response. For alpha2 macroglobulin a strong positive association with HGF and a negative correlation with TGF-beta1 serum concentrations were observed.

In contrast, for haptoglobin, a strong and positive correlation was observed with TGF-beta1. In experimental fibrosis, it has been observed that transduction with the HGF gene suppressed the increase of TGF-beta1 and that HGF stimulates synthesis of alpha2-macroglobulin and decreases synthesis of haptoglobin. Therefore, it seems that these two proteins are very informative, being representative of the two main fibrogenesis cytokines: alpha2-macroglobulin is representative of HGF and haptoglobin is representative of TGF-beta1.

GGT has been several times observed associated with fibrosis and used in association with prothrombin and apoliporotein A1 PGA index (7–8, 13–14, 34). In this study the diagnostic value of GGT was independent of other factors, particularly transaminases and bilirubin. No explanation can currently be given for the independent diagnostic value of total serum bilirubin in non cirrhotic patients. Both GGT and bilirubin were associated with HGF. Besides early cholestasis, an increase of epidermal growth factor could be one explanation for the GGT increase.

Gamma globulin serum concentration has been associated with cirrhosis and porto-systemic shunts for years (36). In this study, it was shown that, although lower than in patients with cirrhosis, gamma-globulin concentration was already increased in patients with non cirrhotic fibrosis in comparison to patients with F1 or F0.

ApoA1 serum concentration has been several times observed associated with fibrosis and used in association with prothrombin and GGT: PGA index (cf. supra). No significant additive diagnostic value of apo-AII or apoB in comparison to apoA1 alone was found in this study.

An unexpected decrease in serum TGF-beta1 according to fibrosis stage was observed in this study, although it did not add significant diagnostic value to the combination of the 6 markers. The strongest correlation was observed between TGF-beta1 and alpha2-microglobulin (R=0.42 p<0.001), which suggests that haptoglobin could be a simple marker of TGF-β1 activation in chronic hepatitis C.

Finally, assessments of serum cytokines did not add significant diagnostic values to the biochemical markers which are easier and cheaper to measure. Measurements of electrophoresis compounds (alpha2-globulins and gamma-globulins) can be viewed as old fashioned semi-quantitative assessments. Their replacement by haptoglobin in a five markers function gave similar predictive values.

In conclusion, the present invention presents a combination of five, six or more biochemical markers to be used for the detection of liver fibrosis and/or presence of inflammatory lesions. The markers used in the present invention had never been combined in such a way, with the age and gender of the patients to give such a good predictive value, as illustrated by the area under the ROC curve.

The diagnosis method of the invention can be analyzed automatically, after an automatic measurement of the values of the markers, and can advantageously be applied for patients with chronic hepatitis C to reduce the indication of liver biopsy.

TABLE 1

Characteristics of included patients for determination of functions f1-a, f2, f3, f4

| Characteristics | Training period | Validation period | Total |
|---|---|---|---|
| Number of patients | 206 | 156 | 362 |
| Age at biopsy (years) mean 95% CI | 47 (45–49) | 48 (46–50) | 47 (46–49) |
| Male (%) | 108 (52%) | 103 (66%) | 211 (58%) |
| Female (%) | 99 (48%) | 53 (34%) | 152 (42%) |
| No fibrosis (F0) | 36 (17%) | 28 (18%) | 64 (18%) |
| Portal fibrosis (F1) | 91 (44%) | 61 (39%) | 152 (42%) |
| Few septa (F2) | 41 (20%) | 29 (19%) | 70 (19%) |
| Many septa (F3) | 18 (9%) | 11 (7%) | 29 (8%) |
| Cirrhosis (F4) | 21 (10%) | 27 (17%) | 48 (13%) |
| None (A0) | 52 (25%) | 27 (17%) | 79 (22%) |
| Mild (A1) | 87 (42%) | 87 (56%) | 174 (48%) |
| Moderate (A2) | 63 (30%) | 38 (24%) | 101 (28%) |
| Severe (A3) | 5 (2%) | 4 (3%) | 9 (2%) |
| Iron score | 1.2 (0.8–1.6) | 1.4 (0.9–1.7) | 1.3 (1.0–1.6) |
| Steatosis (%) | 12% (9–26%) | 15% (10–19%) | 13% (10–16%) |
| Markers (normal range) | | | |
| AST U/L (17–27 female) (20–32 male) | 71 (63–80) | 79 (65–92) | 74 (67–82) |
| ALT U/L (11–26 female) (16–35 male) | 108 (95–121) | 113 (92–133) | 110 (99–122) |
| Total Bilirubin umoles/L (2–17) | 11 (10–12) | 13 (9–18) | 12 (10–14) |
| Albumin g/L (35–44) | 44 (43–44) | 44 (43–45) | 44 (43–44) |
| GGT U/L (7–32 female) (11–49 male) | 81 (64–98) | 99 (72–126) | 89 (74–104) |
| Alpha2 macroglobulin g/L (female 1.6–4.0 male 1.4–3.3) | 2.6 (2.5–2.7) | 2.5 (2.3–2.6) | 2.6 (2.5–2.7) |
| Alpha1 globulin g/L(1–3) | 1.9 (1.9–2.0) | 1.8 (1.8–1.9) | 1.9 (1.9–1.9) |
| Alpha2 globulin g/L (4–9) | 7.6 (7.4–7.8) | 6.8 (6.6–7.1) | 7.3 (7.1–7.4) |
| Beta globulin g/L (4–10) | 6.8 (6.7–7.0) | 7.0 (6.8–7.2) | 6.9 (6.8–7.0) |
| Gamma globulin g/L (5–12) | 14.9 (14.3–15.6) | 14.6 (13.8–15.5) | 14.8 (14.3–15.3) |
| ApoA1 g/L (1.2–1.7) | 1.5 (1.5–1.6) | 1.4 (1.4–1.5) | 1.5 (1.4–1.5) |
| ApoB g/L (0.5–1.4) | ND | 0.9 (0.8–0.9) | ND |
| ApoA2 g/L (0.3–0.5) | ND | 0.3 (0.3–0.3) | ND |
| IL 10 pg/ml (<16) | ND | 73 (41–105) | ND |
| TGF B1 ng/l (35–64) | ND | 32 (29–33) | ND |

ND: Not determined

TABLE 2

Diagnostic value (aera under the ROC curves ± sd) of biochemical markers for significant fibrosis (Few F2, Many septa F3, Cirrhosis F4), for f1-a, f2, for the patients of Table 1.

| | Training period | | Validation period | | Both periods | |
|---|---|---|---|---|---|---|
| Markers | Area under ROC curve | Significance Logistic regression | Area under ROC curve | Significance Logistic regression | Area under ROC curve | Significance Logistic regression |
| AST | 0.774 ± 0.04 | 0.13 | 0.706 ± 0.04 | 0.35 | 0.743 ± 0.03 | 0.35 |
| Alpha2 macroglobulin | 0.753 ± 0.04 | <0.001 | 0.750 ± 0.04 | <0.001 | 0.751 ± 0.03 | <0.001 |
| ALT | 0.724 ± 0.04 | 0.09 | 0.583 ± 0.05 | 0.11 | 0.662 ± 0.03 | 0.41 |
| GGT | 0.680 ± 0.04 | 0.03 | 0.722 ± 0.04 | 0.01 | 0.700 ± 0.03 | 0.003 |
| Gamma globulin | 0.680 ± 0.04 | 0.16 | 0.680 ± 0.04 | 0.59 | 0.676 ± 0.03 | 0.04 |
| Total Bilirubin | 0.611 ± 0.04 | 0.69 | 0.751 ± 0.04 | 0.008 | 0.673 ± 0.03 | 0.06 |
| Albumin | 0.485 ± 0.04 | 0.12 | 0.326 ± 0.04 | 0.53 | 0.415 ± 0.03 | 0.68 |
| Alpha1 globulin | 0.512 ± 0.04 | 0.30 | 0.571 ± 0.05 | 0.80 | 0.534 ± 0.03 | 0.26 |
| Alpha2 globulin | 0.488 ± 0.04 | 0.007 | 0.482 ± 0.05 | 0.03 | 0.480 ± 0.03 | <0.001 |
| Beta globulin | 0.477 ± 0.04 | 0.75 | 0.578 ± 0.05 | 0.45 | 0.522 ± 0.03 | 0.97 |
| ApoA1 | 0.449 ± 0.04 | 0.14 | 0.372 ± 0.04 | 0.12 | 0.413 ± 0.03 | 0.05 |
| Logistic function of 10 markers and age and sex | 0.856 ± 0.03 | <0.001 $R^2 = 0.314$ | 0.885 ± 0.03 | <0.001 $R^2 = 0.363$ | 0.853 ± 0.02 | <0.001 $R^2 = 0.310$ |

TABLE 2-continued

Diagnostic value (aera under the ROC curves ± sd) of biochemical markers for significant fibrosis (Few F2, Many septa F3, Cirrhosis F4), for f1-a, f2, for the patients of Table 1.

| | Training period | | Validation period | | Both periods | |
|---|---|---|---|---|---|---|
| Markers | Area under ROC curve | Significance Logistic regression | Area under ROC curve | Significance Logistic regression | Area under ROC curve | Significance Logistic regression |
| Logistic function of 6 markers and age and sex* | 0.839 ± 0.03 | <0.001 $R^2 = 0.288$ | 0.868 ± 0.03 | <0.001 $R^2 = 0.347$ | 0.851 ± 0.02 | <0.001 $R^2 = 0.298$ |

*Logistic function of 6 markers and age and sex: 6.826 × LogAlpha2Macroglobulin (g/l) − 0.479 × Alpha2Globulin (g/l) + 1.252 × LogGGT (IU/l) + 0.0707 × Gamma (g/l) + 0.0273 × Age (in years) + 1.628 × LogBilirubin (umol/l) − .925 × ApoA1 (g/l) + 0.344 × Sex (female = 0, male = 1) − 4.544.
ND: Not determined
$R^2$ = R squared

TABLE 3

Sensitivity, Specificity and predictive value of the six markers fibrosis function f1-a

| Cutoff of fibrosis function | Sensitivity | Specificity | Likelihood Ratio | Prev = 0.40 PPV | Prev = 0.40 NPV | Prev = 0.10 PPV | Prev = 0.10 NPV | Prev = 0.90 PPV | Prev = 0.90 NPV |
|---|---|---|---|---|---|---|---|---|---|
| 0.10 | 0.99 | 0.30 | 1.41 | 0.49 | 0.97 | 0.14 | 0.995 | 0.93 | 0.71 |
| 0.20 | 0.91 | 0.52 | 1.89 | 0.56 | 0.90 | 0.17 | 0.98 | 0.94 | 0.39 |
| 0.30 | 0.83 | 0.65 | 2.35 | 0.61 | 0.85 | 0.21 | 0.97 | 0.96 | 0.30 |
| 0.40 | 0.74 | 0.74 | 2.85 | 0.66 | 0.81 | 0.24 | 0.96 | 0.96 | 0.24 |
| 0.50 | 0.67 | 0.81 | 3.62 | 0.71 | 0.79 | 0.29 | 0.96 | 0.97 | 0.22 |
| 0.60 | 0.59 | 0.93 | 8.48 | 0.85 | 0.77 | 0.49 | 0.95 | 0.99 | 0.20 |
| 0.70 | 0.51 | 0.96 | 12.16 | 0.89 | 0.74 | 0.57 | 0.95 | 0.99 | 0.18 |
| 0.80 | 0.32 | 0.98 | 13.90 | 0.90 | 0.68 | 0.61 | 0.93 | 0.99 | 0.14 |
| 0.90 | 0.16 | 0.995 | 35.50 | 0.96 | 0.64 | 0.80 | 0.91 | 0.997 | 0.12 |

TABLE 4

Characteristics of included patients for determination of logistic functions f1-b and f5.

| Characteristics | Training period | Validation period | Total |
|---|---|---|---|
| Number of patients | 205 | 134 | 339 |
| Age at biopsy (years) mean 95% CI | 47 (45–49) | 48 (46–50) | 47 (46–49) |
| Male (%) | 108 (53%) | 88 (66%) | 196 (58%) |
| Female (%) | 97 (47%) | 46 (34%) | 143 (42%) |
| No fibrosis (F0) | 36 (17%) | 20 (15%) | 56 (17%) |
| Portal fibrosis (F1) | 91 (44%) | 54 (40%) | 145 (43%) |
| Few septa (F2) | 40 (20%) | 28 (21%) | 68 (20%) |
| Many septa (F3) | 18 (9%) | 10 (7%) | 28 (8%) |
| Cirrhosis (F4) | 20 (10%) | 22 (17%) | 42 (12%) |
| None (A0) | 52 (25%) | 17 (12%) | 69 (20%) |
| Mild (A1) | 85 (41%) | 80 (60%) | 165 (49%) |
| Moderate (A2) | 63 (31%) | 33 (25%) | 96 (28%) |
| Severe (A3) | 5 (2%) | 4 (3%) | 9 (3%) |
| Iron score | 1.2 (0.8–1.6) | 1.4 (0.9–1.7) | 1.3 (1.0–1.6) |
| Steatosis (%) | 12% (9–26%) | 15% (10–19%) | 13% (10–16%) |
| Markers (normal range) | | | |
| AST UI/L (17–27 female) (20–32 male) | 71 (63–80) | 79 (65–92) | 77 (67–82) |
| ALT UI/L (11–26 female) (16–35 male) | 108 (95–121) | 113 (92–133) | 114 (99–122) |
| Total Bilirubin umoles/L (2–17) | 11 (10–12) | 13 (9–18) | 12 (10–14) |
| Albumin g/L (35–44) | 44 (43–44) | 44 (43–45) | 44 (43–44) |
| GGT U/L (7–32 female) (11–49 male) | 81 (64–98) | 99 (72–126) | 88 (74–104) |
| Alpha2 macroglobulin g/L (female 1.6–4.0 male 1.4–3.3) | 2.6 (2.5–2.7) | 2.5 (2.3–2.6) | 2.6 (2.5–2.7) |
| Alpha1 globulin g/L (1–3) | 1.9 (1.9–2.0) | 1.8 (1.8–1.9) | 1.9 (1.9–1.9) |
| Alpha2 globulin g/L (4–9) | 7.6 (7.4–7.8) | 6.8 (6.6–7.1) | 7.3 (7.1–7.4) |
| Beta globulin g/L (4–10) | 6.8 (6.7–7.0) | 7.0 (6.8–7.2) | 6.9 (6.8–7.0) |
| Gamma globulin g/L (5–12) | 14.9 (14.3–15.6) | 14.6 (13.8–15.5) | 14.8 (14.3–15.3) |
| ApoA1 g/L (1.2–1.7) | 1.5 (1.5–1.6) | 1.4 (1.4–1.5) | 1.5 (1.4–1.5) |
| ApoB g/L (0.5–1.4) | ND | 0.9 (0.8–0.9) | ND |
| ApoA2 g/L (0.3–0.5) | ND | 0.3 (0.3–0.3) | ND |
| IL 10 pg/ml (<16) | ND | 78 (41–105) | ND |
| TGF B1 ng/ml (35–64) | ND | 31 (29–33) | ND |

TABLE 4-continued

Characteristics of included patients for determination of logistic functions f1-b and f5.

| Characteristics | Training period | Validation period | Total |
|---|---|---|---|
| Haptoglobin g/l (0.35–2.00)* | 0.97 (0.89–1.05) | 0.89 (0.80–0.99) | 0.94 (0.88–1.00) |
| HGF ng/l (–) | ND | 1181 (976–1386) | ND |

ND: Not determined
*For Haptoglobin, dosage was missing for 8 patients in the first period and one patient in the second period.

TABLE 5

Diagnostic value (aera under the ROC curves ± sd) of biochemical markers for significant fibrosis (Few F2, Many septa F3, Cirrhosis F4), for f1-b, f2, f5, for the patients of Table 4.

| Markers | Training period | | Validation period | | Both periods | |
|---|---|---|---|---|---|---|
| | Area under ROC curve | Significance Logistic regression | Area under ROC curve | Significance Logistic regression | Area under ROC curve | Significance Logistic regression |
| AST | 0.773 ± 0.04 | 0.13 | 0.679 ± 0.05 | 0.35 | 0.739 ± 0.03 | 0.35 |
| Alpha2 Macroglobulin | 0.749 ± 0.04 | <0.001 | 0.740 ± 0.04 | <0.001 | 0.746 ± 0.03 | <0.001 |
| ALT | 0.725 ± 0.04 | 0.09 | 0.564 ± 0.05 | 0.11 | 0.664 ± 0.03 | 0.41 |
| Haptoglobin (decrease)§ | 0.704 ± 0.04 | 0.02 | 0.654 ± 0.05 | 0.006 | 0.685 ± 0.03 | 0.02 |
| Gamma Globulin | 0.680 ± 0.04 | 0.16 | 0.670 ± 0.04 | 0.59 | 0.672 ± 0.03 | 0.04 |
| GGT | 0.672 ± 0.04 | 0.03 | 0.705 ± 0.04 | 0.01 | 0.697 ± 0.03 | 0.003 |
| Total Bilirubin | 0.611 ± 0.04 | 0.69 | 0.726 ± 0.04 | 0.008 | 0.669 ± 0.03 | 0.06 |
| ApoA1 (decrease) | 0.554 ± 0.04 | 0.14 | 0.647 ± 0.05 | 0.12 | 0.597 ± 0.03 | 0.05 |
| Albumin (decrease) | 0.514 ± 0.04 | 0.12 | 0.662 ± 0.04 | 0.53 | 0.574 ± 0.03 | 0.68 |
| Alpha1 Globulin | 0.518 ± 0.04 | 0.30 | 0.577 ± 0.05 | 0.80 | 0.538 ± 0.03 | 0.26 |
| Alpha2 Globulin (decrease) | 0.508 ± 0.04 | 0.007 | 0.518 ± 0.05 | 0.03 | 0.518 ± 0.03 | <0.001 |
| Beta Globulin | 0.475 ± 0.04 | 0.75 | 0.601 ± 0.05 | 0.45 | 0.527 ± 0.03 | 0.97 |
| 10 markers, age and sex Logistic function | 0.856 ± 0.03 | <0.001 $R^2 = 0.314$ | 0.885 ± 0.03 | <0.001 $R^2 = 0.363$ | 0.851 ± 0.02 | <0.001 $R^2 = 0.305$ |
| 6 markers, age and sex Logistic function* | 0.836 ± 0.03 | <0.001 $R^2 = 0.284$ | 0.870 ± 0.03 | <0.001 $R^2 = 0.338$ | 0.847 ± 0.02 | <0.001 $R^2 = 0.297$ |
| 5 markers, age and sex Logistic function** | 0.827 ± 0.03 | <0.001 $R^2 = 0.265$ | 0.851 ± 0.03 | <0.001 $R^2 = 0.323$ | 0.837 ± 0.02 | <0.001 $R^2 = 0.279$ |

§Haptoglobin was retrospectively assessed. Dosage was missing for 8 patients in the first period and one patient in the second period. Significance in logistic regression when haptoglobin replaced alpha2 globulin
*Logistic function of 6 markers and age and sex: 6.552 × LogAlpha2Macroglobulin (g/l) – 0.458 × Alpha2 Globulin (g/l) + 1.113 × LogGGT (IU/l) + 0.0740 × Gamma Globulin (g/l) + 0.0295 × Age (in years) + 1.473 × LogBilirubin (umol/l) – .979 × ApoA1 (g/l) + 0.414 × Sex (female = 0, male = 1) – 4.305.
**Logistic function of 5 markers and age and sex: 4.467 × LogAlpha2Macroglobulin (g/l) – 1.357 × LogHaptoglobin (g/l) + 1.017 × LogGGT (IU/l) + 0.0281 × Age (in years) + 1.737 × LogBilirubin (umol/l) – 1.184 × ApoA1 (g/l) + 0.301 × Sex (female = 0, male = 1) – 5.540.
ND: Not determined
$R^2$ = R squared

TABLE 6

Sensitivity, Specificity and predictive value of the six markers fibrosis function f1-b

| Cut off of fibrosis function | Sensitivity | Specificity | Likelihood Ratio | Prevalence Observed = 0. | | Prevalence Simulated = 0.10 | | Prevalence Simulated = 0.90 | |
|---|---|---|---|---|---|---|---|---|---|
| | | | | PPV | NPV | PPV | NPV | PPV | NPV |
| 0.10 | 0.98 | 0.33 | 1.46 | 0.50 | 0.96 | 0.14 | 0.99 | 0.93 | 0.63 |
| 0.20 | 0.91 | 0.53 | 1.94 | 0.57 | 0.90 | 0.18 | 0.98 | 0.95 | 0.39 |
| 0.30 | 0.81 | 0.65 | 2.33 | 0.62 | 0.83 | 0.21 | 0.97 | 0.95 | 0.28 |
| 0.40 | 0.73 | 0.74 | 2.78 | 0.66 | 0.80 | 0.24 | 0.96 | 0.96 | 0.23 |
| 0.50 | 0.68 | 0.85 | 4.42 | 0.75 | 0.79 | 0.33 | 0.96 | 0.98 | 0.23 |
| 0.60 | 0.60 | 0.93 | 8.64 | 0.86 | 0.77 | 0.49 | 0.95 | 0.99 | 0.21 |
| 0.70 | 0.50 | 0.95 | 10.05 | 0.87 | 0.73 | 0.53 | 0.94 | 0.99 | 0.17 |
| 0.80 | 0.33 | 0.98 | 13.11 | 0.90 | 0.68 | 0.59 | 0.93 | 0.99 | 0.12 |
| 0.90 | 0.17 | 0.99 | 17.48 | 0.92 | 0.64 | 0.66 | 0.92 | 0.997 | 0.12 |

REFERENCES

1. Perrillo R P. Hepatology 1997;26:57S–61S.
2. Consensus Statement. EASL International Consensus Conference on Hepatitis C. J Hepatol 1999; 30: 956–961.
3. Friedman S L. Am J Med. 1999;107:27S–30S.
4. Poynard T, et al. Fibrosis in patients with chronic hepatitis C: detection and significance. Semin Liver Dis 2000;20: 47–55.
5. Poynard T, Lebrec D. The inconvenience of investigations used in hepatology: patients' and hepatologists' opinions. Liver 1982;2:369–75.
6. Poynard T, et al. Appropriateness of liver biopsy. Can J Gastroenterol 2000; 14:543–548.
7. Teare J P, et al. Comparison of serum procollagen III peptide concentrations and PGA index for assessment of hepatic fibrosis. Lancet. 1993;342:895–8.
8. Naveau S, et al. Alpha-2-macroglobulin and hepatic fibrosis. Diagnostic interest. Dig Dis Sci. 1994;39:2426–32.
9. Guechot J, et al. Diagnostic accuracy of hyaluronan and type III procollagen amino-terminal peptide serum assays as markers of liver fibrosis in chronic viral hepatitis C evaluated by ROC curve analysis. Clin Chem. 1996 ;42:558–63.
10. Gabrielli G B, et al. Serum laminin and type III procollagen in chronic hepatitis C. Diagnostic value in the assessment of disease activity and fibrosis. Clin Chim Acta. 1997;265:21–31.
11. Kasahara A, et al. J Hepatol. 1997;26:574–83.
12. Poynard T, Bedossa P. Age and platelet count: a simple index for predicting the presence of histological lesions in patients with antibodies to hepatitis C virus. METAVIR and CLINIVIR Cooperative Study Groups. J Viral Hepat 1997;4: 199–208.
13. Oberti F, et al. Noninvasive diagnosis of hepatic fibrosis or cirrhosis. Gastroenterology. 1997; 113:1609–16.
14. Pilette C, et al. Histopathological evaluation of liver fibrosis: quantitative image analysis vs semi-quantitative scores. Comparison with serum markers. J Hepatol. 1998 ;28:439–46.
15. Wong V S, et al. Serum hyaluronic acid is a useful marker of liver fibrosis in chronic hepatitis C virus infection. J Viral Hepat. 1998;5:187–92.
16. Poynard T, et al. Natural history of liver fibrosis progression in patients with chronic hepatitis C. The OBSVIRC, METAVIR, CLINIVIR, and DOSVIRC groups. Lancet 1997;349:825–32.
17. Doumas B T, et al. Albumin standards and the measurement of serum albumin with bromocresol green. Clin. Chim. Acta 1971, 31, 87–96.
18. The METAVIR cooperative group. Inter- and intraobserver variation in the assessment of liver biopsy of chronic hepatitis C. Hepatology 1994;20; 1:15–20.
19. Bedossa P, Poynard T. An algorithm for the grading of activity in chronic hepatitis C. The METAVIR Cooperative Study Group. Hepatology 1996;24(2):289–93.
20. Hintze J L. NCSS 97 User Guide. Number Cruncher Statistical Systems, Kaysville, Utah 1997.
21. Neural Connection 1.0 User's guide. SPSS. Chicago. Ill. 1995.
22. Poynard T, et al. Randomised trial of interferon alpha2b plus ribavirin for 48 weeks or for 24 weeks versus interferon alpha2b plus placebo for 48 weeks for treatment of chronic infection with hepatitis C virus. International Hepatitis Interventional Therapy Group (IHIT). Lancet 1998;352:1426–32.
23. Boulanger P, et al. Les protéines du plasma sanguin In: Polonovski M, Biochimie Médicale, fascicule III.Masson et compagnie, 1971, Paris, pages 47–154.
24. Tiggelman A M, et al. Localization of alpha 2-macroglobulin protein and messenger RNA in rat liver fibrosis: evidence for the synthesis of alpha 2-macroglobulin within Schistosoma mansoni egg granulomas. Hepatology 1996;23:1260–7
25. Tiggelman A M, et al. Transforming growth factor-beta-induced collagen synthesis by human liver myofibroblasts is inhibited by alpha2-macroglobulin. J Hepatol. 1997; 26:1220–8
26. Meisse D, et al. Cell swelling increased the alpha2-macroglobulin gene expression in cultured rat hepatocytes. FEBS Letter. 1998;422:346–8.
27. Kawser C A, et al. Rat hepatic stellate cell expression of alpha2-macroglobulin is a feature of cellular activation: implications for matrix remodelling in hepatic fibrosis. Clin Sci. 1998;95:179–86.
28. Van Goor H, et al. Alpha macroglobulins and the low-density-lipoprotein-related protein/alpha-2-macroglobulin receptor in experimental renal fibrosis. Exp Nephrol. 1999 January–February;7(1):35–43.
29. Bacq Y, et al. Decrease of haptoglobin serum level in patients with chronic viral hepatitis C. Gastroenterol Clin Biol 1993;17:364–9.
30. Louagie H K, et al. Haptoglobin polymorphism and chronic hepatitis C. J Hepatol 1996;25:10–4.
31. Guillen M I, et al. The hepatocyte growth factor regulates the synthesis of acute-phase proteins in human hepatocytes: divergent effect on interleukin-6-stimulated genes. Hepatology. 1996;23:1345–52.
32. Moshage H. Cytokines and the hepatic acute phaser response. J Pathol 1997;181:257–66.
33. Shiota G, et al. Hepatocyte growth factor and acute phase proteins in patients with chronic liver diseases. J Med 1995;26:295–308.
34. Poynard T, et al. A simple biological index for detection of alcoholic liver disease in drinkers. Gastroenterology 1991; 100:1397–402.
35. Edwards A M, et al . Modulation of gamma-glutamyl-transpeptidase in normal rat hepatocytes in culture by cell density, epidermal growth factor and agents which alter cell differentiation. Carcinogenesis. 1987;8:1837–42.
36. Sakumoto I, et al. Studies on the relationship between the histological changes and liver cell function or plasma proteins in hepatic diseases. Gastroenterol Jpn. 1976; 1:224–36.
37. Paradis V, et al. Role of liver extracellular matrix in transcriptional and post-transcriptional regulation of apolipoprotein A–I by hepatocytes. Cell Mol Biol. 1996;42: 525–34
38. Sabile A, et al. Hepatitis C virus core protein binds to apolipoprotein AII and its secretion is modulated by fibrates. Hepatology. 1999;30:1064–76.
39. Murawaki Y, et al. Plasma transforming growth factor-beta 1 concentrations in patients with chronic viral hepatitis. J Gastroenterol Hepatol. 1998;13:680–4.
40. Tsai J F, et al. Urinary transforming growth factor beta1 levels in hepatitis C virus-related chronic liver disease: correlation between high levels and severity of disease. Hepatology. 1997;25:1141–6.

What is claimed is:

1. A method for diagnosis of an inflammatory, a fibrotic or a cancerous disease in a patient comprising the steps of:
   a) measuring the values of at least four biochemical markers selected from the group consisting of α2-macroglobulin, AST (aspartate aminotransferase), ALT (alanine aminotransferase), GGT (gammaglutamyl transpeptidase), γ-globulin, total bilirubin, albumin, α1-globulin, α2-globulin, haptoglobin, β-globulin, apoA1, IL-10, TGF-β1, apoA2, and apoB in the serum or plasma of said patient;
b) combining said values through a logistic function including said markers; and
c) analyzing the end value of said logistic function in order to determine the presence of liver fibrosis and/or liver necroinflammatory lesions in said patient.

2. The method of claim 1, wherein the logistic function is obtained through the following method:
a) classification of the patients in different groups according to the extent of their disease;
b) identification of factors which differ significantly between these groups by unidimensional analysis;
c) logistic regression analysis to assess the independent discriminative value of markers for the diagnosis of fibrosis and/or liver necroinflammatory lesions; and
d) construction of the logistic function by combination of these identified independent factors.

3. The method of claim 1, wherein said markers are selected from the group consisting of α2-macroglobulin, AST, ALT, GGT, γ-globulin, total bilirubin, albumin, α1-globulin, α2-globulin, haptoglobin, β-globulin, apoA1, IL10, TGF-β1, apoA2, apoβ.

4. The method of claim 1, wherein the logistic function further takes the age and gender of the patient into account.

5. The method of claim 1, wherein said measured biochemical markers used for diagnosis of fibrosis include α2-macroglobulin, GGT, γ-globulin, total bilirubin, (α2-globulin or haptoglobin) and apoA1.

6. The method of claim 1, wherein said measured biochemical markers used for diagnosis of presence of necroinflammatory lesions include α2-macroglobulin, GGT, γ-globulin, (ALT or AST) and apoA1.

7. The method of claim 1, wherein the logistic function is selected from the group consisting of:

$$f1 = a_1 \times \text{Log} [\alpha2\text{-macroglobulin (g/l)}] - a_2 \times [\alpha2\text{-globulin (g/l)}] + a_3 \times \text{Log} [\text{GGT (IU/l)}] + a_4 \times [\gamma\text{-globulin (g/l)}] + a_5 \times [\text{Age (years)}] + a_6 \times \text{Log} [\text{Bilirubin (umol/l)}] - a_7 \times [\text{ApoA1 (g/l)}] + a_8 \times [\text{Sex (female=0, male=1)}] - a_9, \text{ with}$$

$a_1$ comprised between 6.5 and 6.9,
$a_2$ comprised between 0.450 and 0.485,
$a_3$ comprised between 1.100 and 1.300,
$a_4$ comprised between 0.0700 and 0.0750,
$a_5$ comprised between 0.0265 and 0.0300,
$a_6$ comprised between 1.400 and 1.700,
$a_7$ comprised between 0.900 and 1,
$a_8$ comprised between 0.300 and 0.450, and
$a_9$ comprised between 4.200 and 4.700;

$$f2 = b_1 \times \text{Log} [\alpha2\text{-macroglobulin (g/l)}] - b_2 \times [\alpha2\text{-globulin (g/l)}] + b_3 \times \text{Log} [\text{GGT (IU/l)}] + b_4 \times [\gamma\text{-globulin (g/l)}] + b_5 \times [\text{Age (years)}] + b_6 \times \text{Log} [\text{Bilirubin (umol/l)}] - b_7 \times [\text{ApoA1 (g/l)}] + b_8 \times [\text{Sex (female=0, male=1)}] + b_9 [\text{Albumin (g/l)}] + b_{10} [\alpha1\text{-globulin (g/l)}] - b_{11} [\beta2\text{-globulin (g/l)}] 2.189 - b_{12} \times \text{Log} [\text{ALT (IU/l)}] - b_{13}, \text{ with}$$

$b_1$ comprised between 9.9 and 10.2,
$b_2$ comprised between 0.7 and 0.77,
$b_3$ comprised between 2 and 2.4,
$b_4$ comprised between 0.1 and 0.2,
$b_5$ comprised between 0.04 and 0.07,
$b_6$ comprised between 4 and 4.6,
$b_7$ comprised between 2 and 2.5,
$b_8$ comprised between 0.28 and 0.32,
$b_9$ comprised between 0.025 and 0.04,
$b_{10}$ comprised between 2 and 2.2,
$b_{11}$ comprised between 0.1 and 0.16,
$b_{12}$ comprised between 0.7 and 0.9, and
$b_{13}$ comprised between 12 and 14;

$$f3 = c_1 \times \text{Log} [\alpha2\text{-macroglobulin (g/l)}] - c_2 \times [\beta2\text{-globulin (g/l)}] + c_3 \times \text{Log} [\text{GGT (IU/l)}] + c_4 \times [\gamma\text{-globulin (g/l)}] - c_5 \times [\text{Age (years)}] + c_6 \times \text{Log} [\text{ALT (IU/l)} - c_7 \times [\text{ApoA1 (g/l)}] - c_8 \times [\text{Sex (female=0, male=1)}] - c_9, \text{ with}$$

$c_1$ comprised between 3.45 and 3.65,
$c_2$ comprised between 0.3 and 0.4,
$c_3$ comprised between 0.8 and 1,
$c_4$ comprised between 0.075 and 0.09,
$c_5$ comprised between 0.0015 and 0.003,
$c_6$ comprised between 2.1 and 2.5,
$c_7$ comprised between 1.55 and 1.75,
$c_8$ comprised between 0.35 and 0.45, and
$c_9$ comprised between 4 and 4.6;

$$f4 = d_1 \times \text{Log} [\beta2\text{-macroglobulin (g/l)}] - d_2 \times [\beta2\text{-globulin (g/l)}] + d_3 \times \text{Log} [\text{GGT (IU/l)}] + d_4 \times [\gamma\text{-globulin (g/l)}] + d_5 \times [\text{Age (years)}] d_6 \times \text{Log} [\text{Bilirubin (umol/l)}] - d_7 \times [\text{ApoA1 (g/l)}] + d_8 \times [\text{Sex (female=0, male=1)}] + d_9 \text{Log} [\text{ALT (IU/l)}] - d_{10}, \text{ with}$$

$d_1$ comprised between 5.3 and 6.7,
$d_2$ comprised between 0.45 and 0.5,
$d_3$ comprised between 0.8 and 1.2,
$d_4$ comprised between 0.06 and 0.08,
$d_5$ comprised between 0.0015 and 0.0025,
$d_6$ comprised between 1 and 1.2,
$d_7$ comprised between 1 and 1.2,
$d_8$ comprised between 0.09 and 1.1,
$d_9$ comprised between 1.2 and 1.5, and
$d_{10}$ comprised between 4 and 5;

$$f5 = z_1 \times \text{Log} [\alpha2\text{-macroglobulin (g/l)}] - z_2 \times \text{Log} [\text{Haptoglobin (g/l)}] + z_3 \times \text{Log} [\text{GGT (IU/l)}] + z_4 \times [\text{Age (in years)}] + z_5 \times \text{Log} [\text{Bilirubin (umol/l)}] - z_6 \times [\text{ApoA1 (g/l)}] + z_7 \times \text{Sex (female=0, male=1)} - z_8, \text{ with}$$

$z_1$ comprised between 4 and 5,
$z_2$ comprised between 1.2 and 1.5,
$z_3$ comprised between 0.9 and 1.1,
$z_4$ comprised between 0.0026 and 0.03,
$z_5$ comprised between 1.6 and 1.9,
$z_6$ comprised between 1 and 1.3,
$z_7$ comprised between 0.25 and 0.35, and
$z_8$ comprised between 5 and 6.

8. The method of claim 7, wherein the logistic function is selected from the group consisting of:

$$f1\text{-}a = 6.826 \times \text{Log} [\alpha2\text{-macroglobulin (g/l)}] - 0.479 \times [\alpha2\text{-globulin (g/l)}] + 1.252 \times \text{Log} [\text{GGT (IU/l)}] + 0.0707 \times [\gamma\text{-globulin (g/l)}] + 0.0273 \times [\text{Age (years)}] + 1.628 \times \text{Log} [\text{Bilirubin (umol/l)}] - 0.925 \times [\text{ApoA1 (g/l)}] + 0.344 \times [\text{Sex (female=0, male=1)}] - 4.544;$$

$$f1\text{-}b = 6.552 \times \text{Log} [\alpha2\text{-macroglobulin (g/l)}] - 0.458 \times [\alpha2\text{-globulin (g/l)}] + 1.113 \times \text{Log} [\text{GGT (IU/l)}] + 0.0740 \times [\gamma\text{-globulin (g/l)}] + 0.0295 \times [\text{Age (years)}] + 1.473 \times \text{Log} [\text{Bilirubin (umol/l)}] - 0.979 \times [\text{ApoA1(g/l)}] + 0.414 \times [\text{Sex (female=0, male=1)}] - 4.305;$$

$f2=10.088\times\text{Log}\ [\alpha2\text{-macroglobulin (g/l)}]-0.735\times[\alpha2\text{-globulin (g/l)}]+2.189\times\text{Log [GGT (IU/l)]}+0.137\times[\gamma\text{-globulin (g/l)}]+0.0546\times[\text{Age (years)}]+4.301\times\text{Log [Bilirubin (umol/l)]}-2.284\times[\text{ApoA1 (g/l)}]+0.294\times[\text{Sex (female=0, male=1)}]+0.0312\ [\text{Albumin (g/l)}]+2.109\ [\alpha1\text{-globulin (g/l)}]-0.136\ [\beta2\text{-globulin (g/l)}]-0.813\times\text{Log [ALT (IU/l)]}-13.165;$ $f3=3.513\times\text{Log}\ [\alpha2\text{-macroglobulin (g/l)}]0.354\times[\beta2\text{-globulin (g/l) (g/l)}]+0.889\times\text{Log [GGT (IU/l)]}+0.0827\times[\gamma\text{-globulin (g/l)}]-0.0022\times[\text{Age (years)}]+2.295\times\text{Log [ALT (IU/l)]}1.670\times[\text{ApoA1 (g/l)}]0.415\times[\text{Sex (female=0, male=1)}]4.311;$ $f4=5.981\times\text{Log}\ [\alpha2\text{-macroglobulin (g/l)}]-0.481\times[\alpha2\text{-globulin (g/l)}]+0.965\times\text{Log [GGT (IU/l)]}+0.0679\times[\gamma\text{-globulin (g/l)}]+0.0190\times[\text{Age (years)}]+1.143\times\text{Log [Bilirubin (umol/l)]}-1.097\times[\text{ApoA1 (g/l)}]+0.092\times[\text{Sex (female=0, male=1)}]+1.355\ \text{Log [ALT (IU/l)]}-4.498;$ and $f5=4.467\times\text{Log}\ [\alpha2\text{-macroglobulin (g/l)}]-1.357\times\text{Log [Haptoglobin (g/l)]}+1.017\times\text{Log [GGT (IU/l)]}+0.0281\times[\text{Age (in years)}]+1.737\times\text{Log [Bilirubin (umol/l)]}-1.184\times[\text{ApoA1 (g/l)}]+0.301\times\text{Sex (female=0, male=1)}-5.540.$

9. The method of claim 1, wherein the end value of the logistic function is used for the diagnosis of cirrhosis.

10. The method of claim 1, wherein the end value of the logistic function is used to predict the evolution of the disease.

11. The method of claim 1, wherein the end value of the logistic function is used for the choice of a suitable treatment for the patient.

12. The method of claim 1, wherein the end value of the logistic function is used in the decision of performing a liver biopsy on said patient.

13. The method of claim 1, wherein said patient suffers from a disease involving liver fibrosis, optionally developing to cirrhosis.

14. The method of claim 13, wherein said disease is included in the group consisting of hepatitis B and C, alcoholism, hemochromatosis, metabolic disease, diabetes, obesity, autoimmune liver disease, primary biliary cirrhosis, $\alpha1$-antitrypsin deficit, and Wilson disease.

15. The method of claim 13, wherein said disease is hepatitis C virus infection.

16. A kit for diagnosis of an inflammatory, a fibrotic or a cancerous disease in a patient, comprising: a) instructions for determining the presence of an inflammatory, a fibrotic, or a cancerous disease in said patient; b) reagents for measuring the serum values of the concentrations of at least four biochemical markers selected from the group consisting of $\alpha2$-macroglobulin, AST, ALT, GGT, $\gamma$-globulin, total bilirubin, albumin, $\alpha1$-globulin, $\alpha2$-globulin, haptoglobin, $\beta$-globulin, apoA1, IL10, TGF-$\beta1$, apoA2, and apoB; and c) instructions for using a logistic function that is used to combine said values, in order to obtain an end value, wherein analysis of said end value determines the presence of an inflammatory, a fibrotic, or a cancerous disease in said patient.

* * * * *